United States Patent [19]
Lee et al.

[11] Patent Number: 5,863,865
[45] Date of Patent: Jan. 26, 1999

[54] HERBICIDAL 4-BENZOYLISOXAZOLES DERIVATIVES

[75] Inventors: David L. Lee, Pleasant Hill, Calif.; Nigel Barnes, Berkshire, United Kingdom

[73] Assignee: Zeneca Limited, United Kingdom

[21] Appl. No.: 958,950

[22] Filed: Oct. 28, 1997

[51] Int. Cl.$^6$ .......................... A01N 43/74; C07D 261/10
[52] U.S. Cl. ............................................. 504/271; 548/243
[58] Field of Search ............................. 504/271; 548/243

[56] References Cited

U.S. PATENT DOCUMENTS

| | | | |
|---|---|---|---|
| 5,371,063 | 12/1994 | Cramp et al. | 504/270 |
| 5,371,064 | 12/1994 | Cramp et al. | 504/271 |
| 5,374,606 | 12/1994 | Cramp et al. | 504/270 |
| 5,552,367 | 9/1996 | Gamblin et al. | 504/138 |
| 5,627,131 | 5/1997 | Shribbs | 504/105 |
| 5,658,858 | 8/1997 | Bailey et al. | 504/271 |

FOREIGN PATENT DOCUMENTS

| | | |
|---|---|---|
| 0 418 175 | 3/1991 | European Pat. Off. . |
| 0 487 357 | 5/1992 | European Pat. Off. . |
| 0 527 036 | 2/1993 | European Pat. Off. . |
| 0 527 037 | 2/1993 | European Pat. Off. . |

*Primary Examiner*—Joseph K. McKane
*Attorney, Agent, or Firm*—Marian T. Thomson

[57] ABSTRACT

This invention relates to 4-benzoylisoxazoles of formula (I)

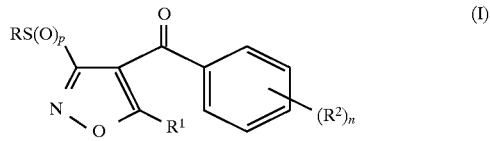

as well as herbicide compositions containing them and their use as herbicides.

24 Claims, No Drawings

HERBICIDAL 4-BENZOYLISOXAZOLES DERIVATIVES

FIELD OF THE INVENTION

This invention relates to 4-benzoylisoxazoles derivatives, herbicide compositions containing them and their use as herbicides.

BACKGROUND OF THE INVENTION

An herbicide is a compound which adversely controls or modifies plant growth, e.g., killing, retarding, defoliating, desiccating, regulating, stunting, tillering, stimulating and dwarfing. The term "plant" refers to all physical parts of a plant, including seeds, seedlings, saplings, roots, tubers, stems, stalks, foliage, and fruits. "Plant growth" includes all phases of development from seed germination to natural or induced cessation of life.

Herbicides are generally used to control or eradicate weed pests. They have gained a high degree of commercial success because it has been shown that such control can increase crop yield and reduce harvesting costs.

A manufacturer of an herbicide generally recommends a range of application rates and concentrations calculated to maximize weed control. The range of rates varies from approximately 0.01 to 50 pounds per acre (0.0111 to 56 kilograms per hectare [kg/ha]), and is usually in the range of from 0.1 to 25 pounds per acre (0.112 to 28 kg/ha). The term "herbicidally effective amount" describes an amount of an herbicide compound which adversely controls or modifies plant growth. The actual amount used depends upon several considerations, including particular weed susceptibility and overall cost limitations. 4-Benzoylisoxazole herbicide compounds have been described in U.S. Pat. Nos. 5,371,063, 5,371,064 and 5,374,606 and in European Patent Publication Nos. 0 418 175, 0 487 357, 0 527 036 and 0 527 037 all incorporated herein by reference. None of these documents however, disclose the advantages of a 3-alkanethio, or an oxidized form thereof, appended to the benzoylisoxazole ring. Surprisingly, the inventors of the instant application have found that the foregoing modification gives the compounds unexpected and advantageous selectivity.

SUMMARY OF THE INVENTION

In one aspect, this invention relates to compounds of formula (I)

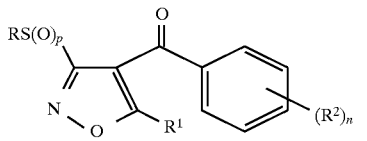

(I)

wherein,

R and $R^1$ which may be the same or different represent a straight- or branched-chain alkyl, alkenyl or alkynyl group containing up to six carbon atoms which is optionally substituted by one or more halogen atoms; a cycloalkyl group containing from three to six carbon atoms optionally substituted by one or more groups $R^5$ or one or more halogen atoms; or optionally substituted phenyl;

$R^2$ represents hydrogen; a halogen atom; a straight- or branched-chain alkyl, alkenyl, alkynyl or alkoxy group containing up to six carbon atoms which is optionally substituted by one or more groups $-OR^5$ or one or more halogen atoms; or a group selected from nitro, cyano, $-CO_2R^3$, $-S(O)XR^6$, $-O(CH_2)_mOR^5$, $-COR^5$, $-NR^{11}R^{12}$, $-(NR^8)SO_2R^7$, $-OR^5$, $-OSO_2R^7$, $-SO_2NR^3R^4$, $-CONR^3R^4$, $-CSNR^3R^4$, $-S(O)_yR^7$ and $-(CR^9R^{10})_t-S(O)_qR^7$;

n represents an integer from one to five; when n is greater than one, the groups $R^2$ may be the same or different;

$R^3$ and $R^4$ each independently represents a hydrogen atom; or a straight- or branched-chain alkyl group containing up to six carbon atoms which is optionally substituted by one or more halogen atoms;

$R^5$ represents a straight- or branched-chain alkyl group containing up to six carbon atoms which is optionally substituted by one or more halogen atoms; a straight- or branched-chain alkenyl or alkynyl group containing from three to six carbon atoms which is optionally substituted by one or more halogen atoms; or phenyl optionally substituted by from one to five groups $R^2$ which may be the same or different;

$R^6$, $R^{11}$ and $R^{12}$, which may be the same or different, each represents a straight- or branched-chain alkyl group containing up to six carbon atoms which is optionally substituted by one or more halogen atoms; or phenyl optionally substituted by from one to five groups $R^2$ which may be the same or different;

$R^7$ represents a straight- or branched-chain alkyl group containing up to six carbon atoms which is optionally substituted by one or more halogen atoms; phenyl optionally substituted by from one to five groups $R^2$ which may be the same or different; $-N$(dimethyl) or a halogen atom;

$R^8$ represents a hydrogen atom; a straight- or branched-chain alkyl, alkenyl or alkynyl group containing up to ten carbon atoms which is optionally substituted by one or more halogen atoms; a cycloalkyl group containing from three to six carbon atoms; phenyl optionally substituted by from one to five groups which may be the same or different selected from halogen, nitro, cyano, $R^5$, $-S(O)_uR^5$ and $-OR^5$; or a group selected from $-SO_2R^6$ and $-OR^5$;

$R^9$ and $R^{10}$, which may be the same or different, each represents a hydrogen atom; a straight- or branched-chain alkyl group containing up to six carbon atoms which is optionally substituted by one or more halogen atoms; or phenyl optionally substituted by from one to five groups $R^2$ which may be the same or different;

p represents zero, one or two;
q represents zero, one or two;
x represents zero, one or two;
u represents zero, one or two;
y represents zero, one or two;
m represents one, two or three;
t represents an integer from one to four; when t is greater than one, the groups $-CR^9R^{10}-$ may be the same or different;

or an agriculturally acceptable salt thereof which possesses herbicidal properties.

In another aspect, the present invention is directed to an herbicidal composition containing (A) a compound of formula (I)

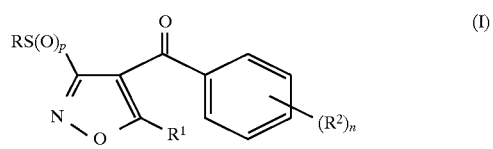

(I)

wherein: R, $R^1$, $R^2$, $R^3$, $R^4$, $R^5$, $R^6$, $R^7$, $R^8$, $R^9$, $R^{10}$, $R^{11}$, $R^{12}$, x, y, u, n, p, q, m and t are as defined above, or an agriculturally acceptable salt thereof; and (B) a carrier therefor.

In yet another aspect, the present invention is directed to a method for controlling undesirable vegetation by applying to an area where such vegetation control is desired an herbicidally effective amount of a compound of formula (I):

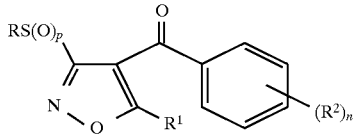

wherein: R, $R^1$, $R^2$, $R^3$, $R^4$, $R^5$, $R^6$, $R^7$, $R^8$, $R^9$, $R^{10}$, $R^{11}$, $R^{12}$, x, y, u, n, p, q, m and t are as defined above, or an agriculturally acceptable salt thereof.

DETAILED DESCRIPTION OF THE INVENTION

The herbicidal 3-(substituted)-4-benzoylisoxazoles of this invention are of the formula (I)

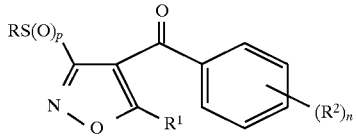

wherein, R, $R^1$, $R^2$, $R^3$, $R^4$, $R^5$, $R^6$, $R^7$, $R^8$, $R^9$, $R^{10}$, $R^{11}$, $R^{12}$, x, y, u, n, p, q, m and t are as defined above, or an agriculturally acceptable salt thereof which possesses herbicidal properties.

In certain cases, the groups R to $R^{12}$ may give rise to optical and/or stereoisomerism. All such forms are embraced by the present invention.

By the term "agriculturally acceptable salts" is meant salts the cations or anions of which are known and accepted in the art for the formation of salts for agricultural or horticultural use. Preferably the salts are water-soluble. Suitable acid addition salts, formed by compounds of formula (I) containing an amino group, include salts with inorganic acids, for example, hydrochlorides, sulphates, phosphates and nitrates and salts with organic acids, for example, acetic acid. Suitable salts formed by compounds of formula (I) which are acidic, i.e., compounds containing one or more carboxy groups, with bases include alkali metal (e.g. sodium and potassium) salts, alkaline earth metal (e.g. calcium and magnesium) salts, ammonium and amine (e.g. diethanolamine, triethanolamine, octylamine, dioctylmethylamine and morpholine) salts.

The term "optionally substituted phenyl" includes phenyl or a phenyl group substituted by one or more groups selected from a halogen atom; a straight- or branched-chain alkyl, alkenyl, alkynyl or alkoxy group containing up to six carbon atoms which is optionally substituted by one or more groups —$OR^5$ or one or more halogen atoms; nitro, cyano, —$CO_2R^3$, —$S(O)_xR^6$, $O(CH_2)_mOR^5$, —$COR^5$, —$NR^{11}R^{12}$, —$N(R^8)SO_2R^7$, —$OR^5$, —$OSO_2R^7$, —$SO_2NR^3R^4$, —$CONR^3R^4$, —$CSNR^3R^4$ or —$S(O)_yR^7$.

One preferred class of compounds of formula (I) are those having the formula

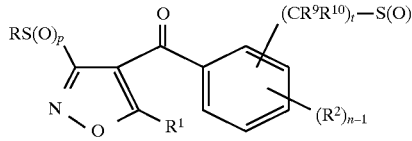

wherein R, $R^1$, $R^2$, $R^7$, $R^9$, $R^{10}$, p, n, q and t have the meanings set forth above.

In a further preferred embodiment where n is greater than one, the benzoyl ring of the compounds of formula (Ia) is 2,4-disubstituted or 2,3,4-trisubstituted. Compounds of formula (Ia) in which n is greater than one and the benzoyl ring of the compound of formula (Ia) is 2,3-disubstituted are also preferred.

A further preferred class of compounds of formula (Ia) are those wherein: R is alkyl; $R^1$ is cyclopropyl; $R^2$ is a halogen atom or a group selected from —$CF_3$, —$S(O)_xMe$, $NO_2$ and —OMe; $R^7$ is a straight- or branched -chain alkyl or alkenyl group containing up to four carbon atoms optionally substituted by from one to three fluorine atoms, or is phenyl; $R^9$ is hydrogen or methyl; $R^{10}$ is hydrogen; and p, x and q, which may be the same or different, each is zero, one or two.

Another preferred class of compounds of formula (I) are compounds having the formula

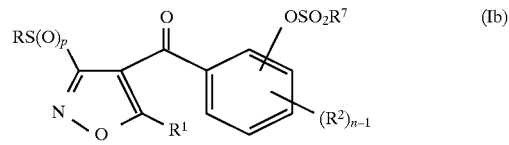

wherein R, $R^1$, $R^2$, $R^7$, p and n have the meanings set forth above.

A further preferred class of compounds of formula (Ib) are those wherein R is alkyl; $R^1$ is ethyl or cyclopropyl; $R^2$ is halogen; and $R^7$ is methyl, ethyl or —$NMe_2$.

Another preferred class of compounds of formula (I) are those having the formula

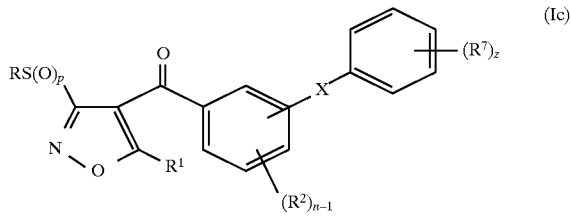

wherein X is oxygen or —$S(O)_q$—; z is zero or an integer from one to five; and R, $R^1$, $R^2$, $R^7$, p and n have the meanings set forth above.

A further preferred class of compounds of formula (Ic) are those wherein one of the substituents of the benzoyl ring is in the 2-position.

Other preferred compounds of formula (Ic) are those wherein the 5- and/or 6-position of the benzoyl ring is unsubstituted, more especially preferred both the 5- and 6-positions are unsubstituted.

A further preferred class of compounds of formula (Ic) are those wherein $R^1$ is a cyclopropyl group; $R^2$ is halogen or a group selected from methyl, trifluoromethyl, methoxy and —$S(O)_pR^6$; X is —$S(O)_q$—; $R^7$ is halogen or a group selected from methyl, trifluoromethyl, nitro and —$OR^5$; $R^5$ is methyl or ethyl; and $R^6$ is methyl.

Another preferred class of compounds of formula (I) are compounds having the formula

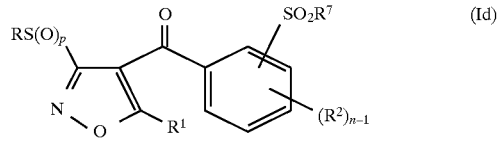

wherein R, $R^1$, $R^2$, $R^7$, p, and n have the meanings set forth above.

A further preferred class of compounds of formula (Id) are those wherein: R is alkyl; $R^1$ is cyclopropyl; $R^2$ is a halogen atom or a group selected from —$CF_3$, —$S(O)_xMe$, $NO_2$ and —OMe; and $R^7$ is a straight- or branched -chain alkyl or alkenyl group containing up to four carbon atoms optionally substituted by from one to three fluorine atoms, or is phenyl. An especially preferred class of compounds of formula (I) have the formula

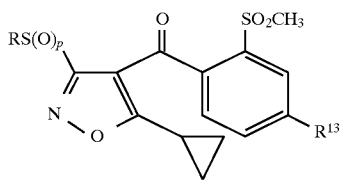

wherein p is defined as above and $R^{13}$ is chlorine, bromine or trifluoromethyl.

Because of their herbicidal properties, compounds of formula (I) wherein $R^1$ is substituted or unsubstituted cyclopropyl are particularly preferred for use in the herbicidal compositions of the present invention.

The following individual compounds are preferred: a) 5-methyl-4-(2-chloro-4-methylsulfonylbenzoyl)-3-methylthioisoxazole b) 5-cyclopropyl-4-(2-nitro-4-trifluoromethylbenzoyl)-3-methylthioisoxazole c) 5-cyclopropyl-4-(2-methyl-3-ethoxy-4-methylsulfonylbenzoyl)-3-methylthioisoxazole; d) 5-cyclopropyl-4-(2-methylsulfonyl-4-trifluoromethylbenzoyl)-3-methylthioisoxazole; and e) 5-cyclopropyl-4-(2-nitro-4-trifluoromethylbenzoyl)-3-methylsulfonylisoxazole.

GENERAL METHOD OF PREPARATION

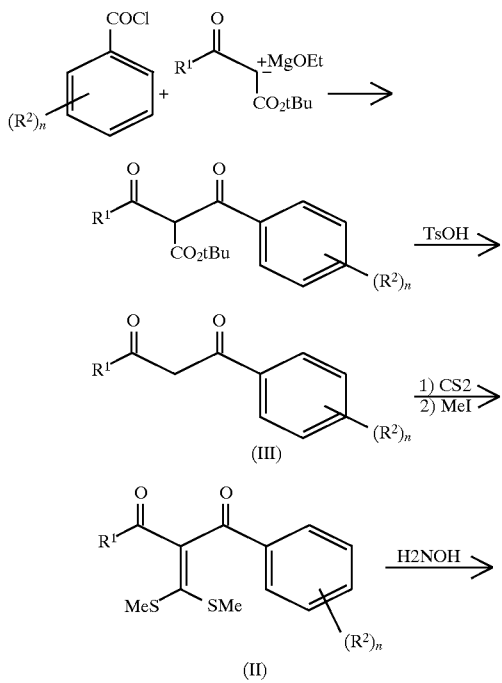

-continued
SCHEME I

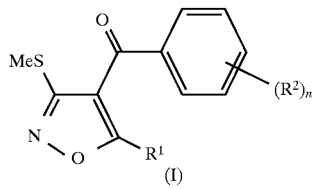

Compounds of formula I may be prepared using the general sequence as shown in Scheme I. In general, a tert-butyl-3-(alkyl)-3-oxopropionate is first reacted with magnesium ethoxide in a nonpolar aprotic solvent such as diethylether. The reaction mixture is heated to reflux and the temperature is maintained for about 1 hour. After allowing the reaction mixture to cool, a substituted benzoic acid chloride is added and allowed to react overnight. The reaction mixture is then poured into ice water and the organic and aqueous phases are separated. The organic phase is dried over magnesium sulfate and then concentrated under reduced pressure to generate a compound of formula IV.

Compounds of formula III may be prepared by reacting a compound of formula IV with 4-toluenesulfonic acid. The reaction is carried out in an organic solvent such as toluene and the mixture is heated to reflux. The temperature is maintained for about 2 hours. The reaction mixture is allowed to cool and is washed with sodium bicarbonate and dried over magnesium sulfate to afford a compound of formula III.

Compounds of formula II may be made by reacting a compound of formula III with anhydrous potassium carbonate in dimethylformamide and carbon disulfide. After about 15 minutes, methyl iodide is added dropwise. The reaction mixture is allowed to stir for about another 3 hours. The mixture is then poured over ice water and the organic layer is dried over magnesium sulfate to generate a compound of formula II.

Compounds of formula I are generated by reacting compounds of formula II with hydroxylamine hydrochloride and sodium acetate. After allowing the mixture to stir overnight at room temperature, the ethanol is removed in vacuo, and the residue partitioned between ethyl ether and water. The ether layer is separated, dried over magnesium sulfate, and concentrated in vacuo to generate a compound of formula I.

FORMULATIONS

The compounds of the present invention are useful as herbicides and can be applied in a variety of ways known to those skilled in the art, at various concentrations. The compounds are useful in controlling the growth of undesirable vegetation by pre-emergent or post-emergent application to the locus where control is desired. The compositions of this invention comprise a compound of formula (I) above and a suitable carrier, which carriers are well known to one of ordinary skill in the art.

In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as wettable powders, as emulsifiable concentrates, as powders or dusts, as flowables, as solutions, suspensions or emulsions, or in controlled-release forms such as microcapsules. These formulations may contain as little as about 0.5% to as much as about 95% or more by weight of active ingredient. The optimum amount for any given compound will depend upon the nature of plants to be controlled. The rate of application will generally vary from about 0.01 to about 11.5 kilograms per hectare, preferably from about 0.02 to about 4.5 kilograms per hectare.

Wettable powders are in the form of finely divided particles which disperse readily in water or other liquid carriers. The particles contain the active ingredient retained in a solid matrix. Typical solid matrices include fuller's earth, kaolin clays, silicas and other readily wettable organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other nonvolatile organic solvents. In use, these concentrates are dispersed in water or other liquid and normally applied as a spray to the area to be treated. The amount of active ingredient may range from about 0.5% to about 95% of the concentrate.

Dusts are free-flowing admixtures of the active ingredient with finely divided solids such as talc, clays, flours and other organic and inorganic solids which act as dispersants and carriers.

Microcapsules are typically droplets or solutions of the active material enclosed in an inert porous shell which allows escape of the enclosed material to the surrounds at controlled rates. Encapsulated droplets are typically about 1 to 50 microns in diameter. The enclosed material typically constitutes about 50 to 95% of the weight of the capsule, and may include solvent in addition to the active compound. Shell of membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as water, acetone, alkylated naphthalenes, xylene and other organic solvents. Pressurized sprayers, wherein the active ingredient is dispersed in finely-divided form as a result of vaporization of a low boiling dispersant solvent carrier may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

Each of the above formulations can be prepared as a package containing the herbicide together with other ingredients of the formulation (diluents, emulsifiers, surfactants, etc.). The formulations can also be prepared by a tank mix method, in which the ingredients are obtained separately and combined at the grower site.

The compounds of the present invention are also useful when combined with other herbicides and/or defoliants, desiccants, growth inhibitors, and the like. These other materials can comprise from about 5% to about 95% of the active ingredients in the formulations. These combinations frequently provide a higher level of effectiveness in controlling weeds and often provide results unattainable with separate formulations of the individual herbicides.

Examples of other herbicides, defoliants, desiccants and plant growth inhibitors with which the compounds of this invention can be combined are:

A. Benzo-2,1,3-thiadiazin-4-one-2,2-dioxides such as bentazone;

B. hormone herbicides, particularly the phenoxyalkanoic acids such as MCPA, MCPA-thioethyl, dichlorprop, 2,4,5-T, MCPB, 2,4-D,2,4-DB, mecoprop, trichlopyr, fluroxypyr, clopyralid, and their derivatives (e.g. salts, esters and amides);

C. pyrazole derivatives such as pyrazoxyfen, pyrazolate and benzofenap;

D. dinitrophenols and their derivatives (e.g. acetates such as DNOC, dinoterb, dinoseb and its ester, dinoseb acetate;

E. dinitroaniline herbicides such as dinitramine, trifluralin, ethalfluralin, pendimethalin; and oryzalin;

F. arylurea herbicides such as diuron, flumeturon, metoxuron, neburon, isoproturon, chlorotoluron, chloroxuron, linuron, monolinuron, chlorobromuron, daimuron, and methabenzthiazuron;

G. phenylcarbamoyloxyphenylcarbamates such as phenmedipham and desmedipham;

H. 2-phenylpyridazin-3-ones such as chloridazon, and norflurazon;

I. uracil herbicides such as lenacil, bromacil and termacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, triallate, diallate, ethyl esprocarb, tiocarbazil, pyridate, and dimepiperate;

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, the corresponding alachlor, the corresponding compound propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, fluroglycofen or salts or esters thereof, nitrofen, bifenox, acifluorfen and salts and esters thereof, oxyfluorfen and fomesafen; chlomitrofen and chlomethoxyfen;

S. phenoxyphenoxypropionate herbicides such as diclofop and esters thereof such the methyl ester, fluazifop and esters thereof, haloxyfop and esters thereof, quizalofop and esters thereof and fenoxaprop and esters thereof such as the ethyl ester;

T. triketone and cyclohexanedione herbicides such as alloxydim and salts thereof, sethoxydim, cycloxydim, sulcotrione, tralkoxydim, and clethodim;

U. sulfonyl urea herbicides such as chlorosulfuron, sulfometuron, metsulfuron and esters thereof; benzsulfuron and esters thereof such as the ester thereof methyl, DPX-M6313, chlorimuron and esters such as the ethyl ester thereof, pirimisulfuron and esters such as the methyl ester thereof, DPX-LS300 and pyrazosulfuron;

V. imidazolidinone herbicides such as imazaquin, imazamethabenz, imazapyr and isopropylammonium salts thereof, imazathapyr;

W. arylanilide herbicides such as flamprop and esters thereof, benzoylpropethyl, diflufenican;

X. amino acid herbicides such as glyphosate and glufosinate and their salts and esters, sulphosate, and bilanafos;

Y. organoarsenical herbicides such as MSMA;

Z. herbicidal amide derivative such as napropamide, propyzamide, carbetamide, tebutam, bromobutide, isoxaben, naproanilide, diphenamid, and naptalam;

AA. 4-benzoylisoxazole and 2-cyano-1,3-dione herbicides.

BB. miscellaneous herbicides including ethofumesate, cinmethylin, difenzoquat and salts thereof such as the methyl sulfate salt, clomazone, oxadiazon, bromofenoxim, barban, tridiphane, flurochloridone, fluthiamide, quinchlorac and mefanacet; and CC. contact herbicides, examples of which include bipyridylium herbicides such as those in which the active entity is paraquat and those in which the active entity is diquat.

These formulations can be applied to the areas where control is desired by conventional methods. Dust and liquid compositions, for example, can be applied by the use of powerdusters, boom and hand sprayers and spray dusters. The formulations can also be applied from airplanes as a dust or a spray or by rope wick applications.

The following are examples of typical formulations:

5% dust:
 5 parts active compound
 95 parts talc

2% dust: 2 parts active compound
 1 part highly dispersed silicic acid
 97 parts talc These dusts are formed by mixing the components then grinding the mixture to the desired particle size.
Wettable powders:
70%:
 70 parts active compound
 5 parts sodium dibutylnaphthylsulfonate
 3 parts naphthalenesulfonic acid/phenolsulfonic acid/ phenol-sulfonic acid/formaldehyde condensate (3:2:1)
 10 parts kaolin
 12 parts Champagne chalk
40%:
 40 parts active compound
 5 parts sodium lignin sulfonate
 1 part sodium dibutylnaphthalene sulfonic acid
 54 parts silicic acid
25%
 25 parts active compound
 4.5 parts calcium lignin sulfate
 1.9 parts Champagne chalk/-hydroxyethyl cellulose (1:1)
 8.3 parts sodium aluminum silicate
 16.5 parts kieselguhr
 46 parts kaolin
10%
 10 parts active compound
 3 parts of a mixture of sodium salts of saturated fatty alcohol sulfates
 5 parts naphthalenesulfonic acid/formaldehyde condensate
 82 parts kaolin These wettable powders are prepared by intimately mixing the active compounds with the additives in suitable mixers, and grinding the resulting mixture in mills or rollers.
Emulsifiable concentrate:
25%
 25 parts active substance
 2.5 parts epoxidized vegetable oil
 10 parts of an alkylarylsulfonate/fatty alcohol polyglycol ether mixture
 57.5 parts xylene The amount of the present compositions which constitute a herbicidally effective amount depends upon the nature of the seeds or plants to be controlled. The rate of application of active ingredients varies from about 0.01 to about 28 kilograms per hectare, preferably about 0.02 to about 11 kilograms per hectare with the actual amount depending on the overall costs and the desired results. It will be readily apparent to one skilled in the art that compositions exhibiting lower herbicidal activity will require a higher dosage than more active compounds for the same degree of control.

EXAMPLE

The following example is intended to further illustrate the present invention and is not intended to limit the scope of this invention in any manner whatsoever.

Example

Compound 3 5-Cyclopropyl-4-(2-methyl-3-ethoxy-4-methylsulfonylbenzoyl)-3-methylthioisoxazole A. 2-tert-Butoxycarbonyl-1-cyclopropyl-3-(2-methyl-3-ethoxy-4-methylsulfonylphenyl)-1,3-propanedione To a stirred solution of tert-butyl 3-cyclopropyl-3-oxopropionate (9.2 g) in ethyl ether (200 mL) was added magnesium ethoxide (5.7 g). The reaction mixture was heated at reflux for 1 hour. After cooling back to room temperature, a solution of 2-methyl-3-ethoxy-4-methylsulfonylbenzoyl chloride (13.8 g), which was prepared from 2-methyl-3-ethoxy-4-methylsulfonylbenzoic acid (the preparation of which is described in U.S. Pat. No. 5,329,041 which is incorporated herein by reference) and oxalyl chloride, in ethyl ether (50 mL) was added over a period of 15 minutes. After stirring overnight at room temperature, the reaction mixture was poured over ice-water (100 mL), and the phases were separated. The ether layer was dried over magnesium sulfate and then concentrated in vacuo to afford 17 g of the crude product as an oil.

B. 1-Cyclopropyl-3-(2-methyl-3-ethoxy-4-methylsulfonylphenyl)-1,3-propanedione

A mixture of crude 2-tert-butoxycarbonyl-1-cyclopropyl-3-(2-methyl-3-ethoxy-4-methylsulfonylphenyl)-1,3-propanedione (10 g) and 4-toluenesulfonic acid (2 g) in dry toluene (150 mL) was stirred and heated at reflux for 2 hours. The cooled mixture was washed with a saturated sodium bicarbonate solution (50 mL), dried over magnesium sulfate, and concentrated in vacuo to afford 7 g of the crude product as a yellow oil.

C. 1-Cyclopropyl-3-(2-methyl-3-ethoxy-4-methylsulfonylphenyl)-2-(2,2-bis-methylethylene)-1,3-propanedione To a mixture of 1-cyclopropyl-3-(2-methyl-3-ethoxy-4-methylsulfonylphenyl)-1,3-propanedione (1.5 g) and anhydrous potassium carbonate (1.9 g) in dimethylformamide at room temperature was added carbon disulfide (0.5 g). After stirring for 15 minutes, methyl iodide (1.4 g) was added dropwise over a period of 15 minutes. After stirring an additional 3 hours, the reaction mixture was poured into a mixture of ethyl ether (100 mL) and ice water (100 mL). The ether layer was separated, dried over magnesium sulfate, and then concentrated in vacuo to afford 2.0 g of the crude product as a yellow solid.

D. 5-Cyclopropyl-4-(2-methyl-3-ethoxy-4-methylsulfonylbenzoyl)-3-methylthioisoxazole To a stirred solution of 1-cyclopropyl-3-(2-methyl-3-ethoxy-4-methylsulfonylphenyl)-2-(2,2-bis-methylthiomethylene)-1,3-propanedione (1.5 g) in ethanol (25 mL) was added hydroxylamine hydrochloride (0.2 g) and sodium acetate (0.3 g). After stirring overnight at room temperature, the ethanol was removed in vacuo, and the residue was partitioned between ethyl ether (50 mL) and water (50 mL). The ether layer was separated, dried over magnesium sulfate, and concentrated in vacuo to afford 1.2 g of the crude title product as a yellow solid.

TABLE I

| Comp. | $R^1$ | R | p | X | Y | Z |
|---|---|---|---|---|---|---|
| 1 | $CH_3$ | $CH_3$ | 0 | Cl | H | $SO_2CH_3$ |
| 2 | cyclopropyl | $CH_3$ | 0 | $NO_2$ | H | $CF_3$ |
| 3 | cyclopropyl | $CH_3$ | 0 | $CH_3$ | $OCH_2CH_3$ | $SO_2CH_3$ |
| 4 | cyclopropyl | $CH_3$ | 0 | $CH_3SO_2$ | H | $CF_3$ |
| 5 | cyclopropyl | $CH_3$ | 2 | $NO_2$ | H | $CF_3$ |

HERBICIDAL SCREENING TESTS

The compounds listed in the foregoing table were tested for herbicidal activity by various methods and at various rates of application. The results of some of these tests are given below. Results obtained in herbicidal screening are affected by a number of factors including: the amount of sunlight, soil type, soil pH, temperature, humidity, depth of planting, plant growth stage, application rate as well as many other factors. All testing procedures are administered with the least amount of variability possible. State of the art equipment and techniques are employed to enable the screening process to remain consistent and reliable.

PRE-EMERGENCE HERBICIDAL SCREENING TEST

On the day preceding treatment, seeds of several different weed species were planted in sandy loam soil containing only trace organic matter. Propagules were sown in individual rows using one species per row across the width of an aluminum flat. Seeding depths ranged from 1.0 to 1.5 cm and plant densities ranged from 3 to 25 plants per row depending on individual plant species.

For the pre-emergence screening test results shown in Table II, the grass weeds planted were green foxtail (*Setaria viridis*) ("SETVI"), wild oat (*Avena fatua*) ("AVEFA"), barnyardgrass (*Echinochloa crusgalli*) ("ECHCG"). Broadleaf weeds utilized were wild mustard (*Sinapis arvensis*) ("SINAR"), velvetleaf (*Abutilon theophrasti*) ("ABUTH") and morningglory (Ipomoea spp.) ("IPOSS"). Additionally, yellow nutsedge (*Cyperus esculentus*) ("CYPES"), nutlets were sown.

Solutions of the test compounds were prepared by weighing out an appropriate amount of the test compound to provide the application rates given [kilograms (acid equivalent) per hectare (kg/ha)], then dissolving the compound in a 50:50 mixture of deionized water and acetone containing 0.5% v/v Tween 20® (polyoxyethylene sorbitan monolaurate emulsifier) as a surfactant. Additional solvents, not exceeding 15% of spray volume, were used if needed to dissolve the compound.

The soil surface was sprayed inside an enclosed linear spray table with the nozzle set above the soil line. The spray table was calibrated to deliver 400 L/ha or 748 L/ha with the application rate as indicated. After treatment, the flats were placed into a greenhouse and watered as needed. The greenhouse environmental systems provided the plants with natural and artificial lighting to attain 14 hours of light per day. Day and night temperatures were maintained at 29° and 21° C., respectively.

The degree of weed control was evaluated and recorded 17–21 days after treatment as a percentage of weed control as compared to the growth of the same species of the same age in an untreated control flat. Percent control is the total injury to the plants due to all factors including: inhibited emergence, stunting, malformation, chlorosis and other types of plant injury. The control ratings range from 0 to 100 percent, where 0 represents no effect with growth equal to the untreated control and where 100 represents complete kill.

POST-EMERGENCE HERBICIDAL SCREENING TEST

The soil was prepared with the same methodology described for the pre-emergence test. The same species used in the pre-emergence test were used in the post emergence testing.

Post-emergence flats were placed in the greenhouse under the same environmental conditions as described for the pre-emergence flats and watered as needed. Plants were grown for 10 to 12 days (or to the appropriate growth stage) prior to compound application. Grasses were sprayed at a 3 to 4 leaf stage and broadleaves at a 1 to 2 leaf stage. Yellow nutsedge was 5 to 7 cm tall at application.

Plants were sprayed 30.5 cm (12 inches) above the foliage with the same spray solution as prepared for the pre-emergence test. The application rate was 0.25 kg/ha. Treated plants were then returned to a greenhouse and watered daily without wetting the foliage. The degree of weed control was evaluated 17–21 days after application and recorded as percentage of control as compared to the growth of the same species in an untreated control flat of the same age. The percent control scale (0–100%) used to evaluate the pre-emergence treatment was also applied to the post-emergence treatment. The post-emergence screening test results are shown in Table III below.

TABLE II

| Comp. No. | Rate (kg/ha) | AVEFA | ECHCG | SETVI | ABUTH | IPOSS | SINAR | CYPES |
|---|---|---|---|---|---|---|---|---|
| 1 | .25 | 0 | 10 | 0 | 10 | 20 | 5 | 0 |
| 2 | .25 | 0 | 100 | 100 | 100 | 60 | 75 | 60 |
| 3 | .25 | 30 | 100 | 100 | 100 | 95 | 100 | 40 |
| 4 | .25 | 80 | 100 | 100 | 100 | 95 | 100 | 50 |
| 5 | .25 | 5 | 98 | 80 | 100 | 20 | 75 | 40 |

TABLE III

| Comp. No. | Rate (kg/ha) | AVEFA | ECHCG | SETVI | ABUTH | IPOSS | SINAR | CYPES |
|---|---|---|---|---|---|---|---|---|
| 1 | .25 | 0 | 5 | 0 | 40 | 60 | 70 | 0 |
| 2 | .25 | 30 | 65 | 10 | 60 | 30 | 35 | 0 |
| 3 | .25 | 25 | 95 | 20 | 100 | 100 | 30 | 5 |
| 4 | .25 | 90 | 95 | 65 | 100 | 100 | 100 | 35 |
| 5 | .25 | 20 | 70 | 15 | 80 | 15 | 5 | 5 |

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A compound of formula (I)

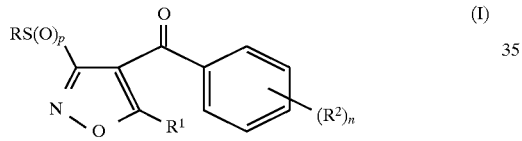

wherein,

R and $R^1$ which may be the same or different represent a straight- or branched-chain alkyl, alkenyl or alkynyl group containing up to six carbon atoms which is optionally substituted by one or more halogen atoms; a cycloalkyl group containing from three to six carbon atoms optionally substituted by one or more groups $R^5$ or one or more halogen atoms; or optionally substituted phenyl;

$R^2$ represents hydrogen; a halogen atom; a straight- or branched-chain alkyl, alkenyl, alkynyl or alkoxy group containing up to six carbon atoms which is optionally substituted by one or more groups —$OR^5$ or one or more halogen atoms; or a group selected from nitro, cyano, —$CO_2R^3$, —$S(O)_xR^6$, —$O(CH_2)_mOR^5$, —$COR^5$, —$NR^{11}R^{12}$, —$N(R^8)SO_2R^7$, —$OR^5$, —$OSO_2R^7$, —$SO_2NR^3R^4$, —$CONR^3R^4$, —$CSNR^3R^4$, —$S(O)_yR^7$ and —$(CR^9R^{10})_t$—$S(O)_qR^7$;

n represents an integer from one to five; when n is greater than one, the groups $R^2$ may be the same or different;

$R^3$ and $R^4$ each independently represents a hydrogen atom; or a straight- or branched-chain alkyl group containing up to six carbon atoms which is optionally substituted by one or more halogen atoms;

$R^5$ represents a straight- or branched-chain alkyl group containing up to six carbon atoms which is optionally substituted by one or more halogen atoms; a straight- or branched-chain alkenyl or alkynyl group containing from three to six carbon atoms which is optionally substituted by one or more halogen atoms; or phenyl optionally substituted by from one to five groups $R^2$ which may be the same or different;

$R^6$, $R^{11}$ and $R^{12}$, which may be the same or different, each represents a straight- or branched-chain alkyl group containing up to six carbon atoms which is optionally substituted by one or more halogen atoms; or phenyl optionally substituted by from one to five groups $R^2$ which may be the same or different;

$R^7$ represents a straight- or branched-chain alkyl group containing up to six carbon atoms which is optionally substituted by one or more halogen atoms; phenyl optionally substituted by from one to five groups $R^2$ which may be the same or different N(dimethyl); or a halogen atom;

$R^8$ represents a hydrogen atom; a straight- or branched-chain alkyl, alkenyl or alkynyl group containing up to ten carbon atoms which is optionally substituted by one or more halogen atoms; a cycloalkyl group containing from three to six carbon atoms; phenyl optionally substituted by from one to five groups which may be the same or different selected from halogen, nitro, cyano, $R^5$, —$S(O)_uR^5$ and —$OR^5$; or a group selected from —$SO_2R^6$ and —$OR^5$;

$R^9$ and $R^{10}$, which may be the same or different, each represents a hydrogen atom; a straight- or branched-chain alkyl group containing up to six carbon atoms which is optionally substituted by one or more halogen atoms; or phenyl optionally substituted by from one to five groups $R^2$ which may be the same or different;

p represents zero, one or two;

q represents zero, one or two;

x represents zero, one or two;

u represents zero, one or two;

y represents zero, one or two;

m represents one, two or three;

t represents an integer from one to four; when t is greater than one the groups —$CR^9R^{10}$— may be the same or different;

or an agriculturally acceptable salt thereof.

2. A compound according to claim 1, wherein:

R and $R^1$ represent a straight- or branched-chain alkyl group containing up to six carbon atoms or a cycloalkyl group containing from three to six carbon atoms;

R[2] represents hydrogen; a halogen atom; a straight- or branched-chain alkyl, or alkoxy group containing up to six carbon atoms which is optionally substituted by one or more groups —OR[5] or one or more halogen atoms; or a group selected from —S(O)$_x$R[6], and —(CR[9]R[10])$_t$—S(O)$_q$R[7]; or an agriculturally acceptable salt thereof.

3. A compound according to claim 1, wherein:

R and R[1] represent a straight- or branched-chain alkyl group containing up to six carbon atoms;

R[2] represents hydrogen; a halogen atom; a straight- or branched-chain alkyl group containing up to six carbon atoms or —OSO$_2$R[7]; and R[7] is methyl ethyl or —N(dimethyl); or an agriculturally acceptable salt thereof.

4. A compound according to claim 1, wherein:

R[2] represents hydrogen; —OR[5] or —SO$_2$R[7]; or an agriculturally acceptable salt thereof.

5. A compound according to claim 1, wherein:

R and R[1] represent a straight- or branched-chain alkyl group containing up to six carbon atoms; or a cycloalkyl group containing from three to six carbon atoms;

R[2] represents hydrogen; a halogen atom; a straight- or branched-chain alkyl, group containing up to six carbon atoms which is optionally substituted by one or more halogen atoms; or —S(O)$_x$R[6]; or an agriculturally acceptable salt thereof.

6. A compound according to claim 1, wherein:

R and R[1] represent a straight- or branched-chain alkyl group containing up to six carbon atoms which is optionally substituted by one or more halogen atoms; or a cycloalkyl group containing from three to six carbon atoms optionally substituted by one or more groups R[5] or one or more halogen atoms;

R[2] may be the same or different and is hydrogen; a halogen atom; a straight- or branched-chain alkyl, alkenyl, alkynyl or alkoxy group containing up to six carbon atoms which is optionally substituted by one or more groups —OR[5] or one or more halogen atoms; or a group selected from —S(O)$_x$R[6], —OR[5], —OSO$_2$R[7], and —S(O)$_y$R[7]; or an agriculturally acceptable salt thereof.

7. A compound according to claim 6, wherein:

R[2] may be the same or different and is selected from the group consisting of hydrogen, halogen, nitro, alkyl, alkoxy haloalkyl, or S(O)$_2$-alkyl; or an agriculturally acceptable salt thereof.

8. A compound according to claim 1 selected from the group consisting of a) 5-methyl-4-(2-chloro-4-methylsulfonylbenzoyl)-3-methylthioisoxazole b) 5-cyclopropyl-4-(2-nitro-4-trifluoromethylbenzoyl)-3-methylthioisoxazole c) 5-cyclopropyl-4-(2-methyl-3-ethoxy-4-methylsulfonylbenzoyl)-3-methylthioisoxazole; d) 5-cyclopropyl-4-(2-methylsulfonyl-4-trifluoromethylbenzoyl)-3-methylthioisoxazole; or e) 5-cyclopropyl-4-(2-nitro-4-trifluoromethylbenzoyl)-3-methylsulfonylisoxazole.

9. An herbicidal composition comprising (A) a compound of formula (I)

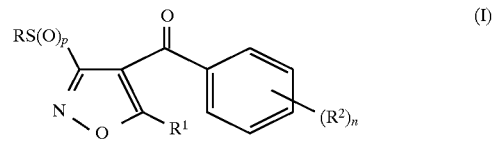

wherein,

R and R[1] which may be the same or different represent a straight- or branched-chain alkyl, alkenyl or alkynyl group containing up to six carbon atoms which is optionally substituted by one or more halogen atoms; a cycloalkyl group containing from three to six carbon atoms optionally substituted by one or more groups R[5] or one or more halogen atoms; or optionally substituted phenyl;

R[2] represents hydrogen; a halogen atom; a straight- or branched-chain alkyl, alkenyl, alkynyl or alkoxy group containing up to six carbon atoms which is optionally substituted by one or more groups —OR[5] or one or more halogen atoms; or a group selected from nitro, cyano, —CO$_2$R[3], —S(O)$_x$R[6], —O(CH$_2$)$_m$OR[5], —COR[5], —NR[11]R[12], —N(R[8])SO$_2$R[7], —OR[5], —OSO$_2$R[7], —SO$_2$NR[3]R[4], —CONR[3]R[4], —CSNR[3]R[4], —S(O)$_y$R[7] and —(CR[9]R[10])$_t$—S(O)$_q$R[7];

n represents an integer from one to five; when n is greater than one, the groups R[2] may be the same or different;

R[3] and R[4] each independently represents a hydrogen atom; or a straight- or branched-chain alkyl group containing up to six carbon atoms which is optionally substituted by one or more halogen atoms;

R[5] represents a straight- or branched-chain alkyl group containing up to six carbon atoms which is optionally substituted by one or more halogen atoms; a straight- or branched-chain alkenyl or alkynyl group containing from three to six carbon atoms which is optionally substituted by one or more halogen atoms; or phenyl optionally substituted by from one to five groups R[2] which may be the same or different;

R[6], R[11] and R[12], which may be the same or different, each represents a straight- or branched-chain alkyl group containing up to six carbon atoms which is optionally substituted by one or more halogen atoms; or phenyl optionally substituted by from one to five groups R[2] which may be the same or different;

R[7] represents a straight- or branched-chain alkyl group containing up to six carbon atoms which is optionally substituted by one or more halogen atoms; phenyl optionally substituted by from one to five groups R[2] which may be the same or different; or a halogen atom;

R[8] represents a hydrogen atom; a straight- or branched-chain alkyl, alkenyl or alkynyl group containing up to ten carbon atoms which is optionally substituted by one or more halogen atoms; a cycloalkyl group containing from three to six carbon atoms; phenyl optionally substituted by from one to five groups which may be the same or different selected from halogen, nitro, cyano, R[5], —S(O)$_u$R[5] and —OR[5]; or a group selected from —SO$_2$R[6] and —OR[5];

R[9] and R[10], which may be the same or different, each represents a hydrogen atom; a straight- or branched-chain alkyl group containing up to six carbon atoms which is optionally substituted by one or more halogen atoms; or phenyl optionally substituted by from one to five groups R[2] which may be the same or different;

p represents zero, one or two;

q represents zero, one or two;

x represents zero, one or two;

u represents zero, one or two;

y represents zero, one or two;

m represents one, two or three;

t represents an integer from one to four; when t is greater than one the groups —$CR^9R^{10}$— may be the same or different;

or an agriculturally acceptable salt thereof; and (B) a carrier therefor.

10. An herbicidal composition according to claim 9, wherein:

R and $R^1$ represent a straight- or branched-chain alkyl group containing up to six carbon atoms or a cycloalkyl group containing from three to six carbon atoms;

$R^2$ represents hydrogen; a halogen atom; a straight- or branched-chain alkyl, or alkoxy group containing up to six carbon atoms which is optionally substituted by one or more groups —$OR^5$ or one or more halogen atoms; or a group selected from —$S(O)_xR^6$, and —$(CR^9R^{10})_t$—$S(O)_qR^7$; or an agriculturally acceptable salt thereof.

11. An herbicidal composition according to claim 9, wherein:

R and $R^1$ represent a straight- or branched-chain alkyl group containing up to six carbon atoms;

$R^2$ represents hydrogen; a halogen atom; a straight- or branched-chain alkyl group containing up to six carbon atoms or —$OSO_2R^7$; and $R^7$ is methyl ethyl or —N(dimethyl); or an agriculturally acceptable salt thereof.

12. An herbicidal composition according to claim 9, wherein:

$R^2$ represents hydrogen; —$OR^5$ or —$SO_2R^7$; or an agriculturally acceptable salt thereof.

13. An herbicidal composition according to claim 9, wherein:

R and $R^1$ represent a straight- or branched-chain alkyl group containing up to six carbon atoms; or a cycloalkyl group containing from three to six carbon atoms;

$R^2$ represents hydrogen; a halogen atom; a straight- or branched-chain alkyl, group containing up to six carbon atoms which is optionally substituted by one or more halogen atoms; or —$S(O)_xR^6$; or an agriculturally acceptable salt thereof.

14. An herbicidal composition acceding to claim 9, wherein:

R and $R^1$ represent a straight- or branched-chain alkyl group containing up to six carbon atoms which is optionally substituted by one or more halogen atoms; or a cycloalkyl group containing from three to six carbon atoms optionally substituted by one or more groups $R^5$ or one or more halogen atoms;

$R^2$ may be the same or different and is hydrogen; a halogen atom; a straight- or branched-chain alkyl, alkenyl, alkynyl or alkoxy group containing up to six carbon atoms which is optionally substituted by one or more groups —$OR^5$ or one or more halogen atoms; or a group selected from —$S(O)_xR^6$, —$OR^5$, —$OSO_2R^7$, and —$S(O)_yR^7$; or an agriculturally acceptable salt thereof.

15. An herbicidal composition according to claim 14, wherein:

$R^2$ is the same or different and is selected from the group consisting of hydrogen, halogen, nitro, alkyl, alkoxy haloalkyl, or $S(O)_2$-alkyl; or an agriculturally acceptable salt thereof.

16. An herbicidal composition according to claim 9, wherein the compound of formula I is selected from the group consisting of a) 5-methyl-4-(2-chloro-4-methylsulfonylbenzoyl)-3-methylthioisoxazole b) 5-cyclopropyl-4-(2-nitro-4-trifluoromethylbenzoyl)-3-methylthioisoxazole c) 5-cyclopropyl-4-(2-methyl-3-ethoxy-4-methylsulfonylbenzoyl)-3-methylthioisoxazole; d) 5-cyclopropyl-4-(2-methylsulfonyl-4-trifluoromethylbenzoyl)-3-methylthioisoxazole; or e) 5-cyclopropyl-4-(2-nitro-4-trifluoromethylbenzoyl)-3-methylsulfonylisoxazole.

17. A method for controlling undesirable vegetation by applying to an area where such vegetation control is desired an herbicidally effective amount comprising a compound of formula (I):

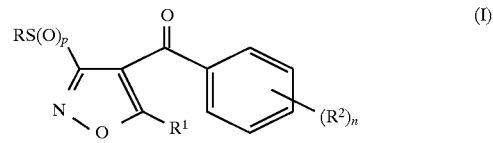

wherein,

R and $R^1$ which may be the same or different represent a straight- or branched-chain alkyl, alkenyl or alkynyl group containing up to six carbon atoms which is optionally substituted by one or more halogen atoms; a cycloalkyl group containing from three to six carbon atoms optionally substituted by one or more groups $R^5$ or one or more halogen atoms; or optionally substituted phenyl;

$R^2$ represents hydrogen; a halogen atom; a straight- or branched-chain alkyl, alkenyl, alkynyl or alkoxy group containing up to six carbon atoms which is optionally substituted by one or more groups —$OR^5$ or one or more halogen atoms; or a group selected from nitro, cyano, —$CO_2R^3$, —$S(O)_xR^6$, —$O(CH_2)_mOR^5$, —$COR^5$, —$NR^{11}R^{12}$, —$N(R^8)SO_2R^7$, —$OR^5$, —$OSO_2R^7$, —$SO_2NR^3R^4$, —$CONR^3R^4$, —$CSNR^3R^4$, —$S(O)_yR^7$ and —$(CR^9R^{10})_t$—$S(O)_qR^7$;

n represents an integer from one to five; when n is greater than one, the groups $R^2$ may be the same or different;

$R^3$ and $R^4$ each independently represents a hydrogen atom; or a straight- or branched-chain alkyl group containing up to six carbon atoms which is optionally substituted by one or more halogen atoms;

$R^5$ represents a straight- or branched-chain alkyl group containing up to six carbon atoms which is optionally substituted by one or more halogen atoms; a straight- or branched-chain alkenyl or alkynyl group containing from three to six carbon atoms which is optionally substituted by one or more halogen atoms; or phenyl optionally substituted by from one to five groups $R^2$ which may be the same or different;

$R^6$, $R^{11}$ and $R^{12}$, which may be the same or different, each represents a straight- or branched-chain alkyl group containing up to six carbon atoms which is optionally substituted by one or more halogen atoms; or phenyl optionally substituted by from one to five groups $R^2$ which may be the same or different;

$R^7$ represents a straight- or branched-chain alkyl group containing up to six carbon atoms which is optionally substituted by one or more halogen atoms; phenyl optionally substituted by from one to five groups $R^2$ which may be the same or different; or a halogen atom;

R[8] represents a hydrogen atom; a straight- or branched-chain alkyl, alkenyl or alkynyl group containing up to ten carbon atoms which is optionally substituted by one or more halogen atoms; a cycloalkyl group containing from three to six carbon atoms; phenyl optionally substituted by from one to five groups which may be the same or different selected from halogen, nitro, cyano, R[5], —S(O)$_u$R[5] and —OR[5]; or a group selected from —SO$_2$R[6] and —OR[5];

R[9] and R[10], which may be the same or different, each represents a hydrogen atom; a straight- or branched-chain alkyl group containing up to six carbon atoms which is optionally substituted by one or more halogen atoms; or phenyl optionally substituted by from one to five groups R[2] which may be the same or different;

p represents zero, one or two;

q represents zero, one or two;

x represents zero, one or two;

u represents zero, one or two;

y represents zero, one or two;

m represents one, two or three;

t represents an integer from one to four; when t is greater than one the groups —CR[9]R[10]— may be the same or different;

or an agriculturally acceptable salt thereof.

18. An method according to claim 17, wherein:

R and R[1] represent a straight- or branched-chain alkyl group containing up to six carbon atoms or a cycloalkyl group containing from three to six carbon atoms;

R[2] represents hydrogen; a halogen atom; a straight- or branched-chain alkyl, or alkoxy group containing up to six carbon atoms which is optionally substituted by one or more groups —OR[5] or one or more halogen atoms; or a group selected from —S(O)$_x$R[6], and —(CR[9]R[10])$_t$—S(O)$_q$R[7]; or an agriculturally acceptable salt thereof.

19. An method according to claim 17, wherein:

R and R[1] represent a straight- or branched-chain alkyl group containing up to six carbon atoms;

R[2] represents hydrogen; a halogen atom; a straight- or branched-chain alkyl group containing up to six carbon atoms or —OSO$_2$R[7]; and R[7] is methyl ethyl or —N(dimethyl); or an agriculturally acceptable salt thereof.

20. A method according to claim 17, wherein:

R[2] represents hydrogen; —OR[5] or —SO$_2$R[7]; or an agriculturally acceptable salt thereof.

21. A method according to claim 17, wherein:

R and R[1] represent a straight- or branched-chain alkyl group containing up to six carbon atoms; or a cycloalkyl group containing from three to six carbon atoms;

R[2] represents hydrogen; a halogen atom; a straight- or branched-chain alkyl, group containing up to six carbon atoms which is optionally substituted by one or more halogen atoms; or —S(O)$_x$R[6]; or an agriculturally acceptable salt thereof.

22. A method according to claim 17, wherein:

R and R[1] represent a straight- or branched-chain alkyl group containing up to six carbon atoms which is optionally substituted by one or more halogen atoms; or a cycloalkyl group containing from three to six carbon atoms optionally substituted by one or more groups R[5] or one or more halogen atoms;

R[2] may be the same or different and is hydrogen; a halogen atom; a straight- or branched-chain alkyl, alkenyl, alkynyl or alkoxy group containing up to six carbon atoms which is optionally substituted by one or more groups —OR[5] or one or more halogen atoms; or a group selected from —S(O)$_x$R[6], —OR[5], —OSO$_2$R[7], and —S(O)$_y$R[7]; or an agriculturally acceptable salt thereof.

23. A method according to claim 22, wherein:

R[2] is the same or different and is selected from the group consisting of hydrogen, halogen, nitro, alkyl, alkoxy haloalkyl, or S(O)$_2$-alkyl; or an agriculturally acceptable salt thereof.

24. A method according to claim 17 wherein formula I is a compound selected from the group consisting of a) 5-methyl-4-(2-chloro-4-methylsulfonylbenzoyl)-3-methylthioisoxazole b) 5-cyclopropyl-4-(2-nitro-4-trifluoromethylbenzoyl)-3-methylthioisoxazole c) 5-cyclopropyl-4-(2-methyl-3-ethoxy-4-methylsulfonylbenzoyl)-3-methylthioisoxazole; d) 5-cyclopropyl-4-(2-methylsulfonyl-4-trifluoromethylbenzoyl)-3-methylthioisoxazole; or e) 5-cyclopropyl-4-(2-nitro-4-trifluoromethylbenzoyl)-3-methylsulfonylisoxazole.

* * * * *

Adverse Decisions In Interference

Patent No.5,863,865, David L. Lee, Nigel Barnes, HERBICIDAL 4-BENZOYLISOXAZOLES DERIVATIVES, Interference No. 104,466, final judgment adverse to the patentees rendered February 27, 2001, as to claims 1-24.

*(Official Gazette March 27, 2001)*